United States Patent [19]

Azam et al.

[11] Patent Number: 4,821,725

[45] Date of Patent: Apr. 18, 1989

[54] DEVICE FOR TREATMENT THROUGH HYPERTHERMIA

[75] Inventors: Guy Azam, La Cella St. Cloud; Guy Convert; Jean M. Cosset, both of Vincennes; Jacques Dufour, Orsay; Jean P. Mabire, Sur Yvette, all of France

[73] Assignee: C.G.R. MeV, Buc, France

[21] Appl. No.: 871,288

[22] Filed: Jun. 6, 1986

[30] Foreign Application Priority Data

Jun. 7, 1985 [FR] France .................... 85 08641

[51] Int. Cl.$^4$ ............................... A61N 1/32
[52] U.S. Cl. ......................... 128/420 A; 128/784;
128/804; 128/422
[58] Field of Search ........... 128/804, 784, 798, 420 R,
128/420 A, 421, 42 R, 423 R

[56] References Cited

U.S. PATENT DOCUMENTS

| 3,895,639 | 7/1975 | Rodler | 128/422 |
|---|---|---|---|
| 4,016,886 | 4/1977 | Doss et al. | 128/784 |
| 4,071,033 | 1/1978 | Nawracaj et al. | 128/420 A |
| 4,346,715 | 8/1982 | Gammell | 128/422 |
| 4,350,168 | 9/1982 | Chable et al. | 128/804 X |
| 4,448,198 | 5/1984 | Turner | 128/422 |
| 4,580,570 | 4/1986 | Sarrell et al. | 128/421 |
| 4,732,161 | 3/1988 | Azam et al. | 128/784 |

FOREIGN PATENT DOCUMENTS 2370484 6/1978 France ........................ 128/804

Primary Examiner—Lee S. Cohen
Attorney, Agent, or Firm—Oblon, Fisher, Spivak, McClelland & Maier

[57] ABSTRACT

The present invention concerns a device for treatment by hyperthermia, comprising unipolar probes of the implantable type, and comprising circuitry for modifying the distribution forms of the electrical field applied to an aera to be treated.

3 Claims, 2 Drawing Sheets

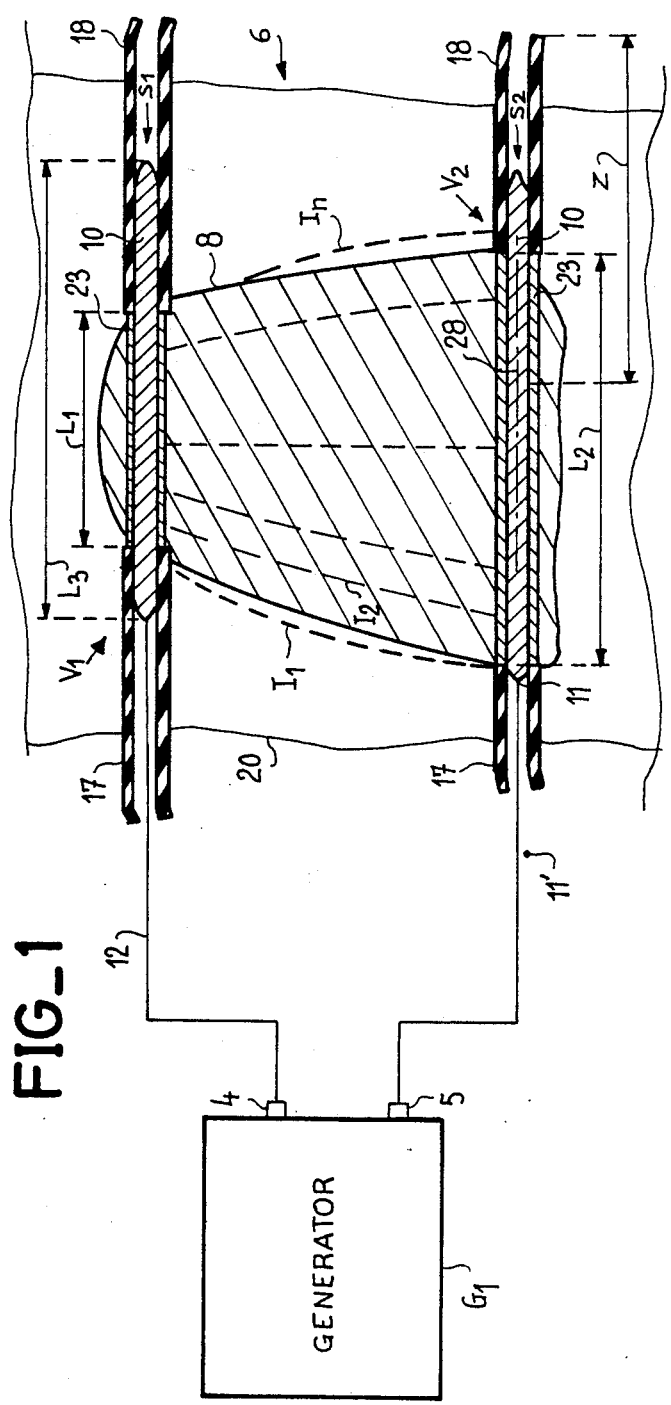
FIG_1
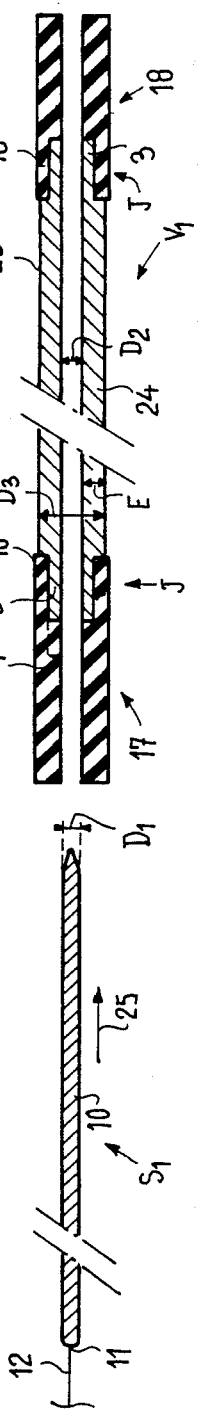
FIG_2

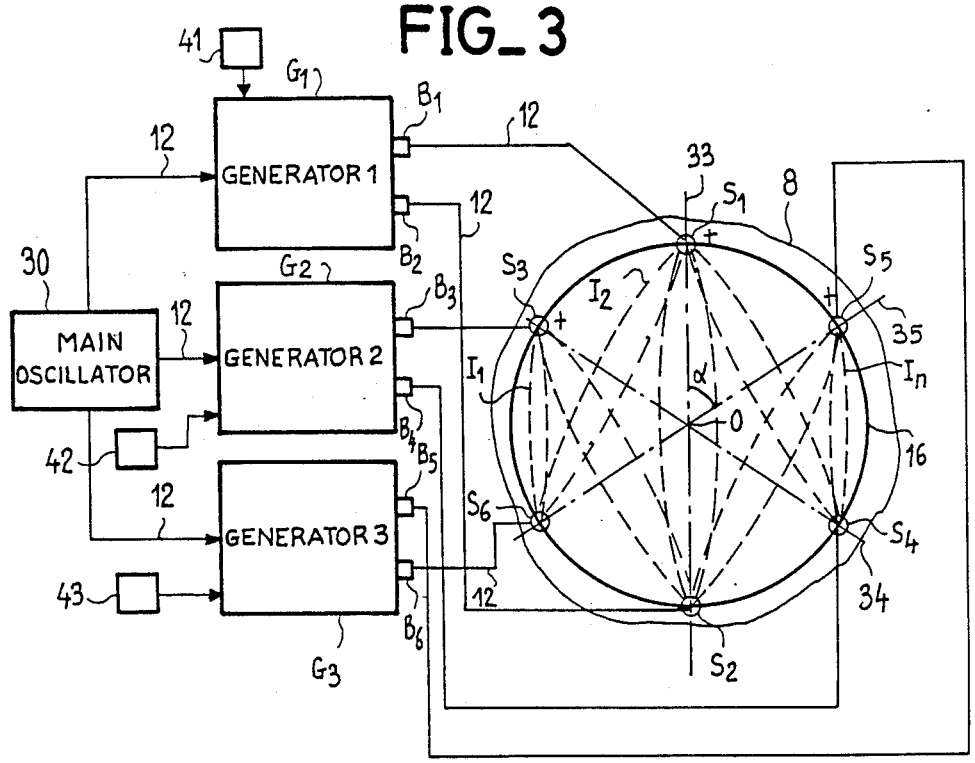
FIG_3
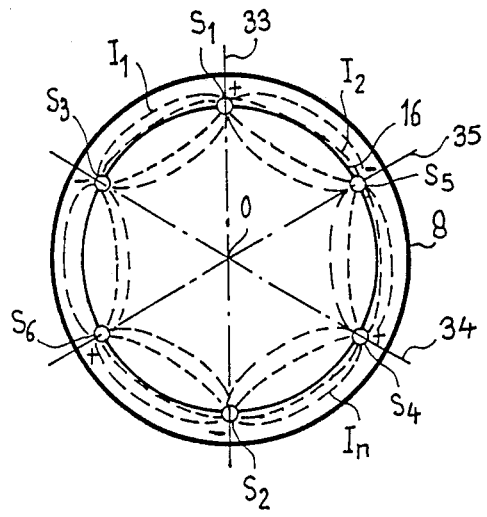
FIG_4

DEVICE FOR TREATMENT THROUGH HYPERTHERMIA

BACKGROUND OF THE INVENTION

1. Field of the invention

The invention concerns a device for treatment by hyperthermia, allowing to heat a diseased area of a patient through dissipation of an electrical energy applied according to an electrical field through use of unipolar electrodes disposed adjacent to the diseased area or within said area. The invention is of particular interest in that it allows to considerably reduce the effects traumatizing for the patient, produced by using such treatments.

2. Summary of the prior art

Hyperthermia is a known process, which consists in heating living biological tissues to temperatures substantially higher than their normal temperature, and which is utilized in the treatment of various illnesses and especially in cancerotherapy. In the example of this latter application, it is desirable to heat the tissues to be treated to temperatures of about 44° C. to 45° C., while avoiding, as much as possible any substantially increase in temperature of the healthy surrounding tissues.

This condition raises a problem which resides in the correct localization of the heated area. In certain configurations which the diseased tissues can present, this correct localization of the heating is impossible to obtain with electrodes situated outside the patient's body. Therefore, in numerous cases, treatment by hyperthermia is carried out through using electrodes directly implanted in or around the area to be treated, so as to more closely confine the heated area.

Such probes can be either of the bipolar or the unipolar type. In the case of bipolar probes, the high frequency electric energy supplied by a generator, in the form of a voltage, can be applied to a single probe of this type, to heat the area in which it is implanted. In the case of unipolar probes, the high or average frequency voltage supplied by the generator is applied to two separate unipolar probes, each of these two probes being connected to one of the output poles of the generator, the heated zone being thus mainly established between two unipolar probes of the type that can be implanted.

The implantation of a bipolar or unipolar probe in a diseased area represents for a patient an operation that can be accompanied by acute pain, and which is particularly traumatizing for treatments by hyperthermia for a given zone to be treated, must generally be repeated at variable frequencies and over periods of time comprised between several days and several tens of days.

It is to be noted that furthermore during treatment, certain tissues of the area to be treated can undergo different rises in temperature, this being able to lead during treatment to modifying the implantation of the probes. Therefore, one of the objects of the invention is to allow to modify the configuration of the heated area, without requiring that the implantation of the probes be modified.

SUMMARY OF THE INVENTION

According to the invention, a device for treatment through hyperthermia which comprises at least one generator supplying an alternating electric energy, the said electric energy being applied, according to an electric field, to an area to be treated of a patient through two unipolar electrodes connected to the said generator, which further comprises a second generator synchronized in frequency with the first generator and connected to third and fourth unipolar electrodes cooperating with the first two unipolar electrodes in order to heat the zone to be treated.

BRIEF DESCRIPTION OF THE DRAWINGS

The invention will become more apparent from the following description given by way of non-limitative illustration with reference to the four appended figures in which:

FIG. 1 illustrates the implanting of unipolar probes in an area to be treated;

FIG. 2 shows details of a vector tube shown in FIG. 1 and adapted to contain a unipolar probe;

FIG. 3 shows schematically a preferred version, with at least two generators, of a treatment device according to the invention allowing to modify the form of distribution of the currents in the zone to be treated;

FIG. 4 illustrates schematically a distribution of the currents as modified with respect to FIG. 3.

DETAILED DESCRIPTION OF THE INVENTION

FIG. 1 illustrates a hyperthermia treatment device 1 according to the invention, and an example of implantation of unipolar probes S1, S2.

The treatment device comprises a generator G1 of the type operating at average or high frequency (in the range of 100 KHz to several MHz), and average power (in the range of several tens of Watt to several hundreds of Watt). The generator G1 supplies, across a first and a second output terminal 4, 5 an alternating electric power adapted to be dissipated within the body 6 (partially represented) of a patient, in order to raise the temperature of an area 8 to be treated by hypethermia. The electric energy supplied by the generator G1, in the form of a voltage (not represented) for example, is applied to the unipolar probes S1, S2, the first unipolar probe S1 being for this purpose connected to the first terminal output 4 and the second unipolar probe S2 being connected to the second output terminal 5. In the non-limitative example described, the unipolar probes S1, S2 are both of the implantable type, i.e. constituted by a metallic needle 10, one end 11 of which is connected to a conventional electrically conductive wire 12 through which they are connected to the generator G1; but it is also known in the prior art, and this can also be applied when carrying out the invention, to use a single implantable probe S1, S2 of the unipolar type cooperating with a unipolar electrode (not represented) adapted to be placed inside the patient's body 6.

In the non-limitative example described, the treatment device 1 furthermore comprises vector tube V1, V2 provided so as to be implanted in the zone 8 to be treated or adjacent thereto, as represented in the non-limitative example of FIG. 1, and to be left there permanently, i.e. over a period of time during which several sessions of treatment by hyperthermia are performed. The vector tubes V1, V2 are adapted to receive, during each treatment session, a unipolar probe S1, S2 introduced into a vector tube V1, V2 through a first or a second end 17, 18 of this latter, at least one of these ends 17, 18 having to be a placed for this purpose outside the patient's body 6, i.e. protruding with respect to the patient's skin 20.

FIG. 2 shows more clearly, by way of non-limitative example, a vector tube V1 and a unipolar probe S1.

The first and second ends 17, 18 of the vector tube V1, at least one of which is necessary, are produced from an electrically insulating material. The first tubular end 17 is extended by a metallic tube 23, communicating with the tubular end 17, so that a unipolar probe S1 can be introduced in the direction shown by the first arrow 25, for example, up to within the metallic tube 23. In the non-limitative example described, the metallic needle 10 of the unipolar probe S1 has a diameter D1 substantially smaller than an internal diameter D2 of the metallic tube 23; this allows to ensure in a simple way an electrical contact between the metallic needle 10 and the metallic tube 23 when the needle is introduced at least partially into this latter. By supposing that the needle 10 has in a conventional way a diameter D1 of about 0.8 mm, and that the internal diameter D2 of the metallic tube 23 is for example about 0.9 to 1 mm, in order to allow the passage of the needle 10 and to ensure the electrical contact and that, on the other hand, the wall 24 of the metallic tube 23 has a thickness E of about 0.1 to 0.15 mm, an external diameter D3 of the metallic tube 23 is about 1.1 to 1.2 mm. The assembly between the metallic tube 23 and the tubular ends 17, 18, can be carried out by those skilled in the art in different ways, as, for example, represented in FIG. 2; where the metallic tube 23 comprises next to its junction J with the tubular ends 17, 18 an end part 3 where the wall 24 has a smaller thickness E1, so that the tubular end 17 can be sunk on this end part 3 without creating any significant overthickness with respect to the external diameter D3; the end part 3 thus comprising an electrically insulating oversheathing 16.

The implantation of the vector tube V1 in the area 8 to be treated can be carried out by using a hollow needle (not represented) of the type called vector cradle, for example, the use of which in the medical field is current, especially for the implantation of various probes in living tissue; said vector cradle is also described in French patent published under No. 2 421 628. The vector tube V1 can be placed in the vector cradle, which is thereafter introduced at the desired site into the zone 8 to be treated; the vector cradle is thereafter withdrawn with care by causing it to slide on the vector tube V1 which remains in place.

Referring again to FIG. 1, the vector tubes V1, V2 being placed in position each unipolar probe S1, S2 is introduced into a vector tube V1, V2. The unipolar probe S1, S2 being connected to the generator G1, and said generator operating, an electrical field represented on FIG. 1 by field lines $I_1, I_2 \ldots I_n$ is established between the unipolar probes S1, S2 through the intermediary of the vector V1, V2 in order to produce a rise in temperature of the area to be treated 8 subjected to the electrical field. One advantage of this disposition resides in the fact that it allows to confer upon vector tubes V1, V2 active length respectively L1, L2 between which is established an electrical field, independently from the lengths L3 of the unipolar probes S1, S2, this allowing to confine more accurately the zone 8 subjected to the electrical field. In fact for frequencies lower than several MHz, thicknesses of insulating materials of about 0.10 mm are sufficient to prevent the establishment of the electric current. In the non-limitative example described, the active lengths L1, L2 correspond to the length of the exposed metallic tubes 23, i.e. not sheathed by the tubular ends 17, 18 of insulating material. This allows in particular to confer active length L1, L2 of possibly different dimensions, compatible with the geometry of the zone 8 to be treated, while using unipolar probes S1, S2 having metallic needles 10 of identical lengths L3.

The tubular ends 17, 18 ensure furthermore protection with respect to the skin 20, which is particularly sensitive to rises in temperature.

Another very important advantage for the patient's comfort is contributed by the flexibility of the tubular ends 17, 18 which allows relative movements thereof with respect to a longitudinal axis 28 of the unipolar probes S1, S2 this flexibility allowing to follow the movements of the skin due for example to slight movements of the patient, thus allowing to avoid that the patient experiences painful sensations.

In the non-limitative example represented in FIG. 1, two vector tubes V1, V2 have been represented but a greater number n of these vector tubes V1, V2 ... Vn can be implanted permanently in the case, for example, where a greater number of unipolar probes S1, S2 are used with example several generators (not represented on FIG. 1) or again in the case where the practitioner desires to modify the heating configuration of a treated zone 8. Such a modification can be desirable from one hyperthermia session to another, or even during the same session, in the case for example where the tissues (not represented) of one zone to be treated 8 have different sensitivies to the electrical field. The modification of the heated zone can thus be carried out by inverting the two unipolar probes of a single generator with respect to the vector tubes in which the probes were placed, in the case where at least two generators each supply two unipolar probes.

FIG. 3 schematically illustrates a preferred version of the treatment device 1 according to the invention, which allows to carry out modifications of the heated area such as mentioned herein-above, without requiring modification of the implanation position of the vector tubes V1, V2 ... already implanted (not represented on FIG. 3 for enhanced clarity) of modification of the position of the implanted probes. It is to be noted that this version of the invention can also be applied in the case of a conventional utilization of implantable unipolar probes, i.e. without utilizing vector tubes V1, V2 .. . V3.

In this preferred version, the treatment device 1 should comprise, further to the first generator G1, at least one supplementary generator G2, i.e. at least two frequency synchronized generators G1, G2.

Therefore, in the non-limitative example described, the treatment device comprises, in addition to the first generator G1, a second and a third generator substantially of the same type as the first generator G1, a number N of generators, higher than 3 can also be used. In the non-limitative example described, the treatment device 1 comprises furthermore a main oscillator 30 connected by connections 31 to each of the generators G1, G2, G3 in order that these latter operate at a single frequency F1 and according to a single phase.

The area 8 to be treated is represented on FIG. 3 by a cross-sectional view in a plane perpendicular to the longitudinal axis 28 shown in FIG. 1. In the example described, six unipolar probes S1, S2 ... S6 are either implanted directly in the area 8 to be treated, or each is placed as in the previous example, in a previously implanted vector tube; the unipolar probes S1, ... S6 being shown in cross-section, they are represented on FIG. 3 by circles. In the non-limitative example described, the unipolar probes S1, . . . S6 are disposed in an area 8 to be treated substantially on a circle 16 having a centre O, through which pass three axes 33, 34, 35 forming between them an angle alpha of about 30°; two unipolar probes S1, . . . S6 connected to the same generator G1, G2, G3 in the non-limitative example described, disposed on a single axis 33, 34, 35 but opposite with respect to the center O. Each of the probes S1, . . . S6 is connected by an electrical conductor 12 to one of the output terminals B1, B2 . . . B6 of a generator G1, G2, G3;

the first and the second probes S1, S2 disposed on the first axis 33 are connected respectively to the first and the second terminal B1, B2 of the first generator G1;

the third and fourth probes S3, S4 disposed on the second axis 34, are connected respectively to a third and fourth output terminal B3, B4 of the second generator G2;

the fifth and sixth probes S5, S6 disposed on the third axis 35, are connected respectively to a fifth and a sixth terminal B5, B6 of the third generator G3.

The three generators G1, G2, G3 operate at an identical frequency F1, and thus by determining the polarities +,− (for a given instant) of the output terminals B1, B2 and B3, B4 and B5, B6 corresponding to each of the generators G1, G2, G3, it is possible to place unipolar probes S1 to S6 corresponding to a desired position in the area 8 to be treated, such as for example shown on FIG. 3, so as to establish the electrical field between these unipolar probes S1 to S6 according to a desired arrangement; this positioning of the probes can be carried out through direct implanatation or by placing each probe in a vector tube as explained herein-above.

Supposing that the first, third and fifth output terminals B1, B3, B5 have a positive polarity +, the second, fourth and sixth output terminals B2, B4, B6 will have a negative polarity −, these +,− polarities being respectively situated at the unipolar probes S1, S3, S5 and S2, S4, S6.

The electrical field represented by the field lines $I_1$ to $I_n$ will in these conditions be established in the whole of the area 8 to be treated.

As mentioned herein-above, it can be desirable to modify the distribution of the electrical field, i.e. the configuration of the heated area. This is possible according to the invention, without causing any supplementary discomfort to the patient, either by substituting the unipolar probes S1, . . . S6 between one another, with respect to the vector tubes, in the case where the latter are used, or by modifying the respective +,− polarity of the probes S1, to S6 by acting on the generators G1, G2, G3 as well in the case where the unipolar probes S1 to S6 are directly implanted in the area 8 to be treated, as in the case where they are disposed in the vector tubes. For this purpose, in the nonlimitative example described each of the generators G1, G2, G3 comprises an inverter device respectively 41, 42, 43 allowing to invert the polarity between two output terminals B1, B2 and B3, B4 and B5, B6 of any single generator G1, G2, G3. The commutation devices 41, 42, 43 can consist of conventional commutating means allowing for example for the first generator G1 to invert the connections (not represented) established between the output terminals B1, B2 and the amplifiers (not represented), conventionally provided on each generator G1, G2, G3. Such an inversion of polarities can be carried out in different ways, all of which are within the scope of those skilled in the art, and can also consists in an inversion of the conducting wires 12 connected to the output terminals B1, B2.

It is also possible through modifying the polarity of the probes S1 to S6, to obtain modification of the distribution form of the electrical field, as form example represented in FIG. 4.

FIG. 4 represents the area 8 to be treated according to a view analogue to that of FIG. 3, i.e. taken in a plane perpendicular to the longitudinal axis 28 shown on FIG. 1, the unipolar probes S1 to S6 occupy the same position as FIG. 3, but comprise different +,− polarities, so that these polarities are successively positive + and negative −. The electrical field represented by the field lines $I_l$, . $I_n$ established between adjacent probes of opposite polarities thus corresponds substantially to a circular distribution around the circumference of circle 16, i.e. around the center O which in this configuration is not subjected to the electrical field.

Other heating configurations of the area 8 to be treated can be obtained, by modifying either the distribution of the probes S1, . . . S6 in the vector tubes V1, V2 . . . or by modifying the positive + or negative − polarity conferred upon each of the probes.

This description constitutes a non-limitative example of a hyperthermia treatment device 1 according to the invention, which allows to distribute the energy adapted to heat an area to be treated according to a form appropriate to this area and possibly to modify this form with a minimum of discomfort to the patient through using means such as, on the one hand, vector tubes V1, V2 . . . Vn in which the unipolar probes can be easily introduced or withdrawn and, on the other hand, commutation means 41, 42, 43 that can be actuated with respect to at least one generator G1, G2, G3.

What is claimed is:

1. A treatment device using hyperthermia, comprising:
    a first generator supplying an alternating electrical energy;
    two unipolar implantable probes connected to the output of said generator to receive said alternating electrical energy and to apply said electrical energy, according to an electric field, to an area of a patient to be treated;
    at least one second generator synchronized in frequency with said first generator;
    a third and fourth unipolar probe connected to receive the output of said at least one second generator and cooperating with said first two unipolar probes in order to heat said area of said patient; and
    means for modifying the distribution forms of said electrical field from said first and said at least one second generator including means for inverting the plus, minus polarity of said electrical energy applied to at least to said two unipolar probes which are connected to said first generator.

2. A treatment device according to claim 1, wherein each of the said generators comprises commutation means for inverting the polarity applied to the two unipolar probes to which it is connected in order to modify the distribution of said electrical field in said are to be treated.

3. A treatment device according to claim 1, further comprising a main oscillator connected to said first and second generators for causing each of said first and second generators to operate at the same frequency.

* * * * *